United States Patent [19]

Tsuji

[11] 4,267,376
[45] May 12, 1981

[54] STEROID SYNTHESIS

[75] Inventor: Jiro Tsuji, Kanagawa, Japan

[73] Assignee: Takeda Chemical Industries, Ltd., Osaka, Japan

[21] Appl. No.: 71,404

[22] Filed: Aug. 30, 1979

[30] Foreign Application Priority Data

Sep. 8, 1978 [JP] Japan .................................. 53-111093

[51] Int. Cl.³ ...................... C07C 45/32; C07C 45/66; C07C 49/643
[52] U.S. Cl. .................................... 568/344; 568/346; 568/347; 568/373
[58] Field of Search ...................... 568/343, 344, 373; 260/586 E

[56] References Cited

U.S. PATENT DOCUMENTS

| | | | |
|---|---|---|---|
| 3,766,248 | 10/1973 | Nedelec et al. | 260/586 E |
| 3,793,374 | 2/1974 | Micheli | 260/586 E |
| 3,979,458 | 9/1976 | Fried | 260/586 E |
| 4,176,123 | 11/1979 | Knight et al. | 260/586 E |

Primary Examiner—Natalie Trousof
Assistant Examiner—Vera C. Clarke
Attorney, Agent, or Firm—Craig & Antonelli

[57] ABSTRACT

A compound having the general formula

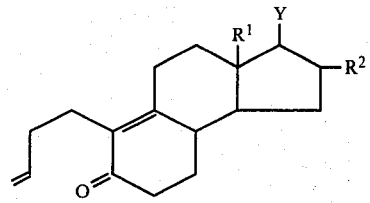

wherein $R^1$ is a lower alkyl group, $R^2$ is hydrogen or a lower alkyl group and Y is a protected hydroxyl group, for example, (±)-3β-tert.butoxy-2,3,3a,4,5,7,8,9,9aβ,-9bα-decahydro-3aβ-methyl-6-(3-butenyl)-1H-benz-(e)inden-7-one, which is an intermediate for steroids, is prepared by dehydrative cyclization of a compound of the general formula

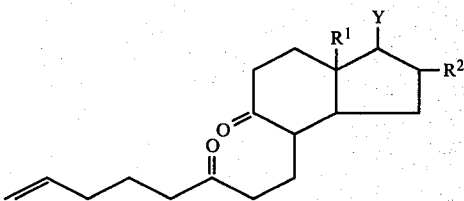

wherein the symbols of $R^1$, Y and $R^2$ are same as defined above.

7 Claims, No Drawings

STEROID SYNTHESIS

This invention relates to intermediates for steroid synthesis and a method for producing same.

Steroids can not only be isolated from natural substances but also be prepared by total synthesis which have been developed in recent years. In particular, methods via the following structure (I) are gathering attention [Angewande Chemie 72 (1960), pp. 725–730]

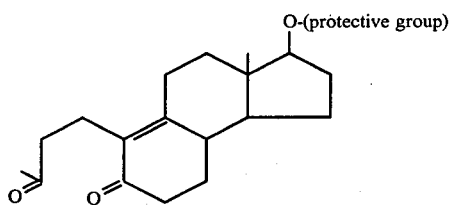

However, synthesis of this intermediate (I) requires a large number of steps, involves the use of expensive starting materials or includes reaction steps which give only poor yield.

The present inventor carried out an intensive research under the circumstances and has discovered a new method for producing in good yield a compound of the general formula (VI). According to the invention, 1,7-octadien-3-one (II), which can be easily obtained from butadiene, is allowed to react with a compound of the general formula (III) to obtain a compound of the general formula (IV), and the ester group is then removed therefrom to obtain a compound of general formula (V). This compound (V) is cyclized to a compound (VI), which is then oxidized in an oxygen-containing atmosphere in the presence of a small amount of water and palladium catalyst with a reoxidizing agent.

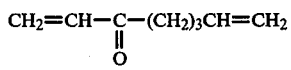

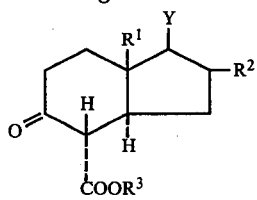

(wherein $R^1$ and $R^3$ each is a lower alkyl group; $R^2$ is hydrogen or a lower alkyl group; Y is a protected hydroxyl group)

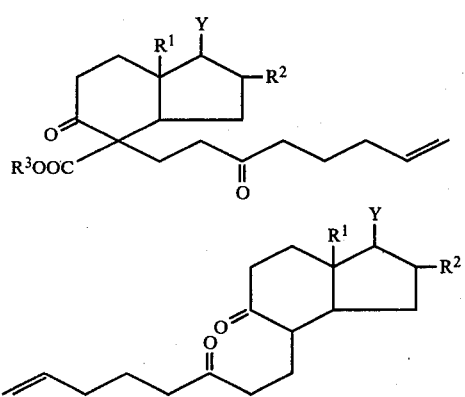

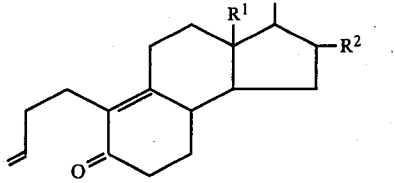

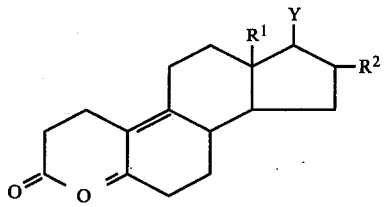

This invention is therefore concerned with:-
(1) a compound of the general formula (VI);
(2) a method of producing a compound of the general formula (VI) wherein a compound of the general formula (V) is dehydratively cyclized; and
(3) a method of producing a compound of the general formula (VII) wherein a compound of the general formula (VI) is oxidized in an oxygen-containing atmosphere in the presence of a small amount of water and a palladium catalyst with a reoxidizing agent.

Referring to the above general formulas, the lower alkyl groups of $R^1$, $R^2$ and $R^3$ mean an alkyl group of 1 to 3 carbon atoms, such as methyl, ethyl, n-propyl or i-propyl. The protective group on protected hydroxyl Y may be any group, as long as it can be removed under mild conditions, e.g. under acidic conditions established by hydrochloric acid, sulfuric acid or the like or by a catalytic reduction. The group may, for example, be tert-butyl, tetrahydropyranyl, benzyl and acetyl.

Compound having the general formula (VI) include:
(1) 3-Tert-butoxy-2,3,3a,4,5,7,8,9,9aβ,9bα-decahydro-3aβ-methyl-6-(3-butenyl)-1H-benz(e)inden-7-one;
(2) 3-Tert-butoxy-2,3,3a,4,5,7,8,9,9aβ,9bα-decahydro-2-methyl-3aβ-methyl-6-(3-butenyl)-1H-benz(e)inden-7-one;
(3) 3-Tert-butoxy-2,3,3a,4,5,7,8,9,9aβ,9bα-decahydro-3aβ-ethyl-6-(3-butenyl)-1H-benz(e)inden-7-one;
(4) 3-Tert-butoxy-2,3,3a,4,5,7,8,9,9aβ,9bα-decahydro-2-ethyl-3aβ-methyl-6-(3-butenyl)-1H-benz(e)inden-7-one;
(5) 3-Tert-butoxy-2,3,3a,4,5,7,8,9,9aβ,9bα-decahydro-3aβ-isopropyl-6-(3-butenyl)-1H-benz(e)inden-7-one.

The 1,7-octadien-3-one (II) can be produced in the following manner. Butadiene is dimerized in the presence of acetic acid to obtain 3-acetoxy-1,7-diene, which is then hydrolyzed to 1,7-octadien-3-ol (Tetrahedron letters 1967, 2451). This 1,7-octadien-3-ol is oxidized with an oxidizing agent such as chromic anhydride, chromic anhydride-pyridine complex, 2,3-dichloro-5,6-dicyano-1,4-benzoquinone (DDQ), manganese dioxide, silver carbonate, copper oxide or the like.

The compound of the general formula (III) can be produced by the method described in Journal of Organic Chemistry 38 (1973), pp. 3239–3243 or 40 (1975), pp. 675–681 or any method analogous thereto. There are various isomers of the compound (III). The compound (III) wherein $R^1$ is β-oriented is desirably employed for the purpose of producing a compound having a natural orientation. Y is also preferably β-oriented. α-Oriented compound can be converted into the natural-type one by oxidation and selective reduction.

In the method of this invention, a condensation reaction between the compounds (II) and (III) is preferably conducted in the presence of a basic compound such as sodium hydride, sodium hydroxide, triethylamine or pyridine. This reaction is desirably conducted in an inert solvent capable of dissolving the starting compound, such as benzene, tetrahydrofuran, dioxane, dimethylformamide, acetonitrile or benzene. Although the reaction proceeds satisfactorily at a temperature below the room temperature, e.g. 0° C.–10° C., it may be carried out at higher or lower temperature, if necessary.

The reaction for removal of the ester group from the compound (IV) is carried out in dimethylformamide, dimethylsulfoxide, hexamethylphosphoramide, sulfolane or the like at an elevated temperature of about 100°–200° C. in the presence of an excess, relative to the ester, of sodium chloride, sodium oxalate, sodium iodide, sodium cyanide, potassium cyanide, potassium iodide or the like.

The cyclization reaction of the compound (V) proceeds readily in the presence of alkali (e.g. sodium hydroxide, potassium hydroxide, sodium ethoxide) or acid (e.g. p-toluenesulfonic acid, HCl, etc.). The reaction is preferably carried out in a solvent such as water, ethanol, propanol, tetrahydrofuran, dioxane, acetonitrile or benzene. When an acid catalyst is used, the reaction may be conducted in a solvent of acetic acid or the like. The reaction may be carried out at room temperature or at an elevated temperature (e.g. under reflux).

The oxidation of the compound (VI) can be conducted in an oxygen-containing atmosphere such as air in the presence of a small amount of water and a palladium catalyst such, for example, as palladium chloride, with a reoxidizing agent selected from the group consisting of a copper compound, e.g. cuprous chloride, cupric chloride or cupric nitrate, an iron compound e.g. ferric chloride and benzoquinone. This reaction may be conducted in the presence of an inert solvent such as dimethylformamide, methanol, ethanol, propanol, sulfolane, dimethoxyethane, dioxane or the like. Although the reaction proceeds satisfactorily at room temperature, it may be conducted at higher or lower temperature if necessary. The reaction is conducted in the presence of oxygen at atmospheric or supratmospheric pressure, preferably with stirring or shaking.

The compound (VII) is of great use as an intermediate for the synthesis of various steroids. The compound (VII) can be further transformed by the method described in Angewande Chemie 72 (1960), pp. 725–730, for instance, into 19-nor-testosterone steroids, estrone steroids, 9,11-dehydrotestosterone steroids, androsterone steroids, cortisone steroids, etc.

REFERENCE EXAMPLE

In 100 cc of carbon tetrachloride is dissolved 3.1 g of 1,7-octadien-3-ol, followed by addition of 10 g of activated manganese dioxide. The mixture is stirred at room temperature for 4 days. The reaction mixture is filtered and the solvent is distilled off under a reduced pressure of 20–30 mm Hg. As a fraction at 30°–32° C./4 mm Hg, there is obtained 2 g of 1,7-octadien-3-one. The above fraction is identified to be 1,7-octadien-3-one by the following analyses.

Infrared spectrometry:
1695 cm$^{-1}$, 1680 cm$^{-1}$, 1640 cm$^{-1}$, 910 cm$^{-1}$
NMR (CCl$_4$):
δ0.9–1.8(4H, methylene)
2.49(2H, triplet, —C$\underline{H}_2$—CO)
4.7–6.3(6H, olefin)

EXAMPLE 1

(1) (±)-Methyl 1-β-tert-butoxy-3aα,4β,5,6,7,7a-hexahydro-4-(3-oxo-7-octenyl)-7aβ-methyl-5-oxo-4-indancarboxylate Ten (10) mg of sodium hydride is added to dry benzene at 0° C. and stirred. To this solution is added methyl (±)-1β-tert-butoxy-3aα,4β,5,6,7,7a-hexahydro-7aβ-methyl-5-oxo-4α-indancarboxylate (496 mg). After a sufficient amount of hydrogen has evolved, 1,7-octadien-3-one (500 mg) is added and stirred at 0° C. for 1.5 hours. Then the mixture is stirred at room temperature for 2 hours, at the end of which time it is neutralized with dilute hydrochloric acid. The organic layer is extracted with methylene chloride, washed with aqueous sodium chloride, dried over magnesium sulfate and filtered. The solvent is then evaporated off and the residue is purified by silica gel column chromatography (ether:hexane=1:4). By the above procedure is obtained 486 mg (68%) of the above-indicated compound. [IR 1710 cm$^{-1}$, 1641 cm$^{-1}$, 908 cm$^{-1}$; NMR (CCl$_4$) 0.89 ppm (3H, singlet, C$\underline{H}_3$ (ring methyl)), 1.10(9H, singlet, OC(CH$_3$)$_3$), 4.65 (3H, singlet, methyl ester), 4.7–6.1(3H, multiplet, vinyl)]

(2) (±)-3a,4,7,7a-Tetrahydro-1-tert-butoxy-4-(3-oxo-7-octenyl)-7aβ-methyl-5(6H)-indanone The ester obtained in (1) (262.5 mg), sodium iodide (250 mg) and water (250 mg) are added to hexamethylphosphoramide (HMPA, 4 ml) and the mixture is stirred for one hour at 150° C. After cooling to room temperature, water (20 ml) is added and the organic layer is extracted with ether. The extract is washed with water and aqueous sodium chloride, dried over magnesium sulfate and filtered. The solvent is then evaporated off and the residue is purified by silica gel column chromatography (ether:hexane=1:6). By the above procedure is obtained 163 mg (75%) of the above-indicated compound. [IR 1710 cm$^{-1}$, 1641 cm$^{-1}$, 908 cm$^{-1}$; NMR (CCl$_4$) δ1.00 ppm (3H, singlet, —C$\underline{H}_3$), 1.10(9H, singlet, OC(C$\underline{H}_3$)$_3$), 3.40 (1H, multiplet,

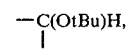

4.6–6.2(3H, multiplet, vinyl)

(3) (±)-3β-tert-butoxy-2,3,3a,4,5,7,8,9,9aβ,9bα-decahydro-3aβ-methyl-6(3-butenyl)-1H-benz(e)inden-7-one Sodium hydroxide (200 mg) is added to a mixture of water (4 ml) and ethanol (2 ml) and the mixture is stirred at room temperature. The diketone obtained in (2) (163 mg) is added to the solution and the mixture refluxed under stirring for one hour. The reaction mixture is poured in dilute hydrochloric acid-ice and the organic layer is extracted with ether. The extract is washed with water and aqueous sodium chloride in that order, dried over magnesium sulfate and filtered. The solvent is evaporated off and the residue is purified by silica gel column chromatography (ether:hexane=1:6). By the above procedure is obtained 112 mg (73%) of the above-indicated compound. [IR 1668 cm$^{-1}$, 1641 cm$^{-1}$, 910 cm$^{-1}$; NMR 0.85 ppm(3H, singlet, —C$\underline{H}_3$), 1.10 (9H, singlet, OC(C$\underline{H}_3$)$_3$), 3.35(1H, multiplet, —C-(OtBu)$\underline{H}$), 4.6–3.1 (3H, multiplet, vinyl)]

(4)
(±)-3β-tert-butoxy-2,3,3a,4,5,7,8,9,9aβ,9bβ-decahydro-3aβ-methyl-6-(3-oxobutyl)-1H-benz(e)inden-7-one Palladium chloride (90 mg), cuprous chloride (500 mg) and water (1 ml) are added to dimethylformamide (10 ml) and the mixture is stirred at room temperature for 2 hours. The olefin obtained in (3) (111.6 mg) is added to the above solution and stirred in an oxygen-containing atmosphere at room temperature for 5 hours. After dilute hydrochloric acid is added, the organic layer is extracted with ether and the extract is washed with water and aqueous sodium chloride in that order, dried over magnesium sulfate and filtered. The solvent is evaporated off and the residue is purified by silica gel column chromatography (ether:hexane=1:4). By the above procedure is obtained 77.7 mg (66%) of the above-indicated compound. [NMR 0.84 ppm (3H, singlet, —C$\underline{H}_3$), 1.10(9H, singlet, OC(C$\underline{H}_3$)$_3$), 2.04(3H, singlet, —COC$\underline{H}_3$), 3.38(1H, multiplet, C(OtBu)$\underline{H}$)]

EXAMPLE 2

(1) The processes (1) and (2) in Example 1 repeated employing optically active methyl 1β-tert-butoxy-3aα,4β,5,6,7,7a-hexahydro-7aβ-methyl-5-oxo-4α-indancarboxylate ([α]$_D^{25}$=+35.1° (C=1.10, CHCl$_3$)) to give the corresponding optically active (+)3a,4,7,7a-tetrahydro-1-tert-butoxy-4(3-oxo-7-octenyl)-7aβ-methyl-5(6H) indanone. Yield: 68.4%. [α]$_D^{25}$=+23.8° (C=0.992, CHCl$_3$)

(2) Thus obtained diketone is treated in the same manner as the process (3) in Example 1 to obtain (−)-3β-tert-butoxy-2,3,3a,4,5,7,8,9,9aβ,9bα-decahydro-3aβ-methyl-6-(3-butenyl)-1H-benz(e)inden-7-one. Yield: 90%. [α]$_D^{25}$=−14.8° (C=0.61, CHCl$_3$)

(3) The oxidation process described in Example 1 (4) is repeated to give (−)-3β-tert-butoxy-2,3,3a,4,5,7,8,9,9aβ,9bα-decahydro-3aβ-methyl-6-(3-oxobutyl)-1H-benz(e)inden-7-one. Yield: 78%. [α]$_D^{25}$=−18.1° (C=1.02, CHCl$_3$).

(4) Thus obtained diketone is reduced its internal double bond using palladium on carbon in ethanol containing triethylamine in 95% yield. [α]$_D^{25}$=−22.5° (C=1.86, CHCl$_3$). The reduced product is subjected to the aldol condensation and hydrolysis of the t-butyl ether group by refluxing in methanolic acid to give (+)-19-nortestosterone in 76% Yield. mg. 110°–111° C., [α]$_D^{25}$=+57.8° (C=0.526, CHCl$_3$).

I claim:
1. A compound of the general formula:

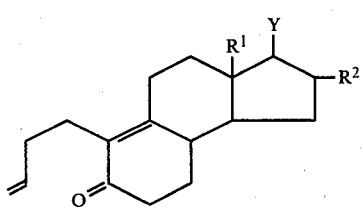

wherein R$^1$ is a lower alkyl group; R$^2$ is hydrogen or a lower alkyl group; Y is a protected hydroxyl group.

2. (±)-3β-tert-butoxy-2,3,3a,4,5,7,8,9,9aβ,9bα-decahydro-3aβ-methyl-6-(3-butenyl)-1H-benz(e)inden-7-one.

3. Method for producing a compound of the general formula:

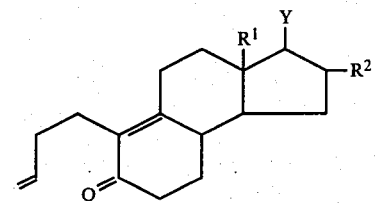

wherein R$^1$ is a lower alkyl group; R$^2$ is hydrogen or a lower alkyl group; Y is a protected hydroxyl group, which comprises subjecting a compound of the general formula:

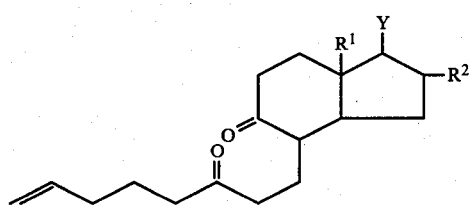

wherein R$^1$, R$^2$ and Y are same as defined above, to dehydrative cyclization reaction in the presence of alkali or acid and in a solvent.

4. Method for producing a compound of the general formula:

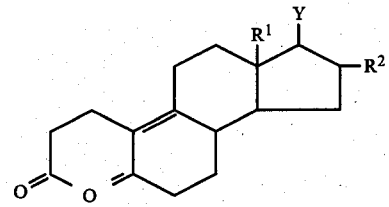

wherein R$^1$ is a lower alkyl group; R$^2$ is hydrogen or a lower alkyl group; Y is a protected hydroxyl group, which comprises subjecting a compound of the general formula:

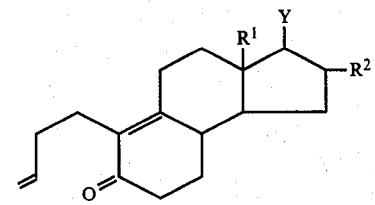

wherein R$^1$, R$^2$ and Y are as defined above, to oxidation in an oxygen-containing atmosphere in the presence of a small amount of water and a palladium catalyst with a reoxidizing agent in the presence of an inert solvent.

5. The method according to claim 3, wherein said reaction is carried out at room temperature or a reflux temperature.

6. The method according to claim 5, wherein the solvent is selected from a group consisting of water, ethanol, propanol, tetrahydrofuran, dioxane, acetonitrile and benzene.

7. The method according to claim 4, wherein said oxygen-containing atmosphere is air, and the inert solvent is selected from the group consisting of dimethylformamide, methanol, ethanol, propanol, sulfolane, dimethoxyethane and dioxane.

* * * * *